(12) United States Patent
Birch et al.

(10) Patent No.: US 8,142,641 B2
(45) Date of Patent: Mar. 27, 2012

(54) ELECTROCHEMICAL SENSOR

(75) Inventors: Stephen William Birch, Whitley Bay (GB); John Sutherland, Bedlington (GB)

(73) Assignee: Palintest Limited, Tyne & Wear (GB)

( * ) Notice: Subject to any disclaimer, the term of this patent is extended or adjusted under 35 U.S.C. 154(b) by 629 days.

(21) Appl. No.: 11/991,191

(22) PCT Filed: Aug. 31, 2006

(86) PCT No.: PCT/GB2006/003223
§ 371 (c)(1),
(2), (4) Date: Apr. 7, 2009

(87) PCT Pub. No.: WO2007/026152
PCT Pub. Date: Mar. 8, 2007

(65) Prior Publication Data
US 2009/0321278 A1    Dec. 31, 2009

(30) Foreign Application Priority Data
Sep. 1, 2005   (GB) .................................. 0517773.8

(51) Int. Cl.
*G01F 1/64* (2006.01)
(52) U.S. Cl. ............... 205/778.5; 205/777.5; 205/779.5; 204/400
(58) Field of Classification Search ................. 205/775, 205/778.5–779.5; 204/435, 400
See application file for complete search history.

(56) References Cited

U.S. PATENT DOCUMENTS

| | | | |
|---|---|---|---|
| 3,902,982 A * | 9/1975 | Nakagawa | 204/406 |
| 4,278,507 A * | 7/1981 | Derreumaux et al. | 205/780 |
| 4,571,292 A | 2/1986 | Liu et al. | |
| 4,655,880 A | 4/1987 | Liu | |
| 5,126,034 A * | 6/1992 | Carter et al. | 204/403.05 |
| 5,739,039 A | 4/1998 | Girault et al. | |
| 5,811,254 A * | 9/1998 | Wu | 435/28 |
| 2001/0042692 A1 | 11/2001 | Gurry et al. | |
| 2006/0073603 A1 * | 4/2006 | Jaunakais | 436/125 |
| 2007/0000777 A1 * | 1/2007 | Ho et al. | 204/403.14 |

FOREIGN PATENT DOCUMENTS

EP    0 352 183 A1    1/1990

OTHER PUBLICATIONS

Potassium Hydrogen Phthalate, Material Safety Data Sheet, National Institute of Standards and Technology, Mar. 11, 2008.*
Prokhorov, G. A.; Kozhevinikov, A. I.; Khomutova, L. Yu, Preparation oand testing of an experimental redoximetric analyzer of residual active chlorine in mine water, Nauchnye Trudy—Vsesoyuznyui Nauchno-Issledovatel'skii i Proektno-Konstruktorskii Institut Okhrany Okruzhushchei Pirodnoi Sredy v Ugol'noi Promyshlennosti, 24, p. 67-72, (1978).*

* cited by examiner

*Primary Examiner* — Jeffrey T Barton
*Assistant Examiner* — Maris R Kessel
(74) *Attorney, Agent, or Firm* — Harness, Dickey & Pierce, P.L.C.

(57) ABSTRACT

A electrochemical sensor comprising a mounting having screen printed array of electrodes located thereon, the array comprising a reference electrode, a counter electrode and a plurality of working electrodes, wherein the working electrodes are each overlaid with an insulating layer of insulating material, the insulating layer having an array of apertures, exposing a respective array of working regions of the working electrodes, and a method of making same by applying screen printing technic, and a method of using same for chlorine determination.

26 Claims, 2 Drawing Sheets

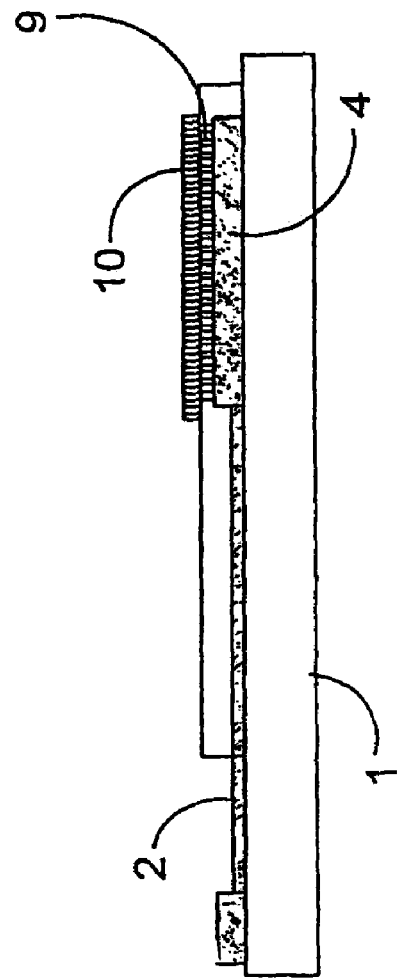
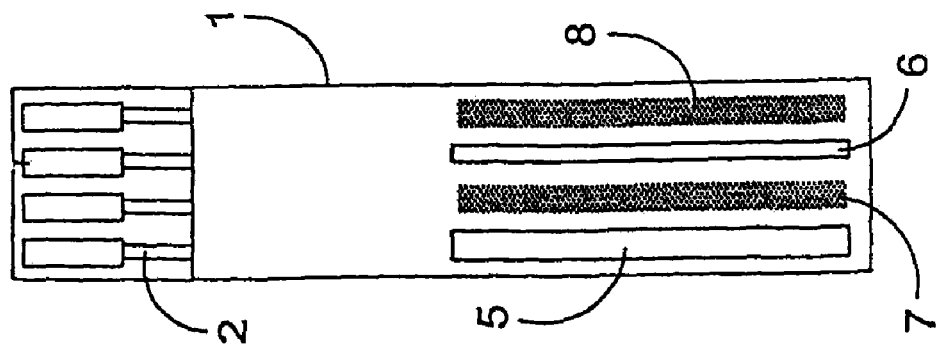
FIGURE 1B
FIGURE 1A

ELECTROCHEMICAL SENSOR

CROSS-REFERENCE TO RELATED APPLICATIONS

This application is a U.S. Stage Application of International application No. PCT/GB2006/003223, filed Aug. 31, 2006, and published in English as WO 2007/026152 A1 on Mar. 8, 2007. This application claims the benefit of Great Britain Application No. 0517773.8, filed Sept. 1, 2005. The disclosure(s) of the above applications are incorporated herein by reference.

This invention relates to an electrochemical sensor for detection of an analyte, particularly but not exclusively for detection of chlorine. The invention also relates to a method of detection of chlorine or other analyte and to a method of manufacture of a sensor for use in performance of the method. In alternative embodiments of the invention, the sensor may detect ammonia.

Chlorine in aqueous solution is a powerful oxidising agent and is used widely for the disinfection of drinking water, recreational water and in the treatment of industrial water. If properly applied, chlorination also provides other benefits such as the removal of colour, taste and odour control, and the prevention of biological growth.

It is essential to control the level of chlorine in water so that the most effective concentration can be maintained. The presence of excess chlorine is detrimental to human and aquatic life and can produce chlorinous tastes and odours in drinking water and unpleasant bathing conditions in swimming pools.

Chlorination may occur by the addition of gaseous chlorine to water or by the addition of sodium hypochlorite. Chlorine rapidly dissolves in water to form hypochlorous acid and hydrochloric acid:

$$Cl_2 + H_2O \Leftrightarrow HCl + HOCl \quad (1)$$

Sodium hypochlorite also reacts to form hypochlorous acid:

$$NaOCl + H_2O \Leftrightarrow NaOH + HOCl \quad (2)$$

The hypochlorous acid partially dissociates to give the hypochlorite ion:

$$HOCl \Leftrightarrow H^+ + OCl^- \quad (3)$$

The three forms of chlorine involved in reactions 1-3, molecular chlorine ($Cl_2$), hypochlorous acid (HOCl) and hypochlorite ion ($OCl^-$) may exist together. Their relative proportions depend upon the pH and temperature. Chlorine in any of these forms is knows ad the "free available residual chlorine".

When free chlorine is added to water, containing ammonia, the hypochlorous acid reacts with the ammonium ion, and depending on the pH, temperature and initial chlorine to ammonia ratio, leads to the formation of monochloramine ($NH_2Cl$), dichloramine ($NHCl_2$) and nitrogen trichloride ($NCl_3$). Chlorine in any of these forms is knows as the "combined available residual chlorine".

Chlorine in the form of HOCl exhibits the greatest bactericidal activity and combined chlorine generally is a much weaker disinfectant. It is therefore important to be able to measure and distinguish between the free and combined forms of chlorine.

There are several laboratory methods for the determination of free and combined chlorine, for example iodometric and amperometric titrations, redox titrations using N,N-diethyl-p-phenylenediamine (DPD) as an indicator, and calorimetric methods using DPD or syringaldazine. However, the chlorine content of water dissipates very quickly and it is important therefore that testing should be done with a minimum of delay and preferably at the point of sampling. A number of portable field test kits have been developed; the most common and widely used is the DPD calorimetric procedure. The reagents are supplied in the form of tablets, powders or liquids and the colour formed by the reaction of free chlorine with DPD is measured spectrophotometrically. Total chlorine can be determined by the further addition of potassium iodide, which induces combined chlorine to react. The combined fraction can then be calculated by the difference between the total and the free chlorine in the sample.

The disadvantages of such a field test include the necessity for the sample to be colour and turbidity free, the use of reagents can introduce errors due to poor mixing, free and combined chlorine must be determined separately and the method is susceptible to a number of interferences.

Free chlorine and total chlorine can be measured electrochemically by applying a voltage to an electrode and measuring the current. Free chlorine can be measured directly; the reaction at the electrode can be represented by:

$$HOCl + 2e^- \rightarrow Cl^- + OH^- \quad (4)$$

Total chlorine (free and combined) can be measured by the addition of potassium iodide, Reactions (5) and (6) show the reaction of potassium iodide with free chlorine and combined chlorine:

$$2I^- + Cl_2 \rightarrow I_2 + 2Cl^- \quad (5)$$

$$2H^+ + NH_2Cl + 2I^- \rightarrow NH_4^+ Cl^- + I_2 \quad (6)$$

The iodine is then reduced to iodide at the electrode.

$$I_2 + 2e^- 2I^- \quad (7)$$

The combined chlorine can then be calculated by the difference in free and total chlorine. Such a system requires reagents to buffer the pH of the test sample, to provide electrolyte and to provide potassium iodide for the measurement of total chlorine. It also requires frequent calibration to correct for drift in the response of the electrode.

WO-A-91/08474 discloses a microelectrode manufactured by use of a photoablation technique to create apertures in a layer of electrically insulating material and allow electrically conducting material exposed through the apertures to create a microelectrode.

According to a first aspect of the present invention, an electrochemical sensor comprises a mounting having a screen printed array of electrodes located thereon, the array comprising a reference electrode, a counter electrode and a plurality of working electrodes, wherein the working electrodes are each overlaid with an insulating layer of insulating material, the insulating layer having an array of apertures exposing a respective array of working regions of the working electrodes.

The sensor is preferably adapted for detection of chlorine, more preferably for the simultaneous measurement of free and total chlorine without requiring use of any additional reagents or for calibration by a user.

Disposable mountings may be provided.

A preferred sensor may comprise a laminar sheet or strip of insulating polymeric material upon which successive layers are applied by screen printing.

In preferred embodiments of the invention, the apertures may have a dimension, or preferably a diameter of about 50-400 μm, preferably about 100-200 μm. Circular apertures are preferred.

In preferred embodiments, the array may comprise 10-500 apertures, preferably 50-200 apertures, more preferably 80-120, most preferably about 95 apertures.

The working electrodes are preferably composed of carbon and may be made by screen printing.

A sensor in accordance with the present invention confers several advantages. A small overall working electrode area may be used so that the total current passed by the electrode is small, making it possible to operate in a solution without addition of a supporting electrolyte. An enhanced rate of mass transport can be achieved using an array of smaller electrodes. Furthermore, a reduction in the double layer capacitance is obtained, leading to an improved level of detection.

A reagent layer may be provided overlying the apertures in the insulating layer. The reagent layer may comprise a porous layer impregnated with one or more reagents adapted to form an electrochemically detectable species when contacted with an analyte. The reagent may comprise a redox indicator that reacts with free chlorine. Alternatively or in addition, the reagent may comprise potassium iodide to react with total chlorine.

Preferred sensors in accordance with this invention do not require addition of reagents to the test solution, for example to determine free and/or total chlorine. Free and total chlorine can be measured simultaneously.

Alternative sensors may be adapted to measurement of ammonia by electro-deposition of a conducting polymer e.g. polypyrrole, polyaniline or polythiophene on the carbon working electrode or the printing of a conducting polymer containing ink as the working electrode.

The reagent may be deposited in the reagent layer by printing or microdosing.

The invention is further described by means of example, but not in any limitative sense, with reference to the accompanying drawings, of which:

FIG. 1(a) is a plan view of a screen-printed sensor in accordance with the present invention;

FIG. 1(b) is a cross-section of a working electrode of a sensor shown in FIG. 1.

Figure 2:
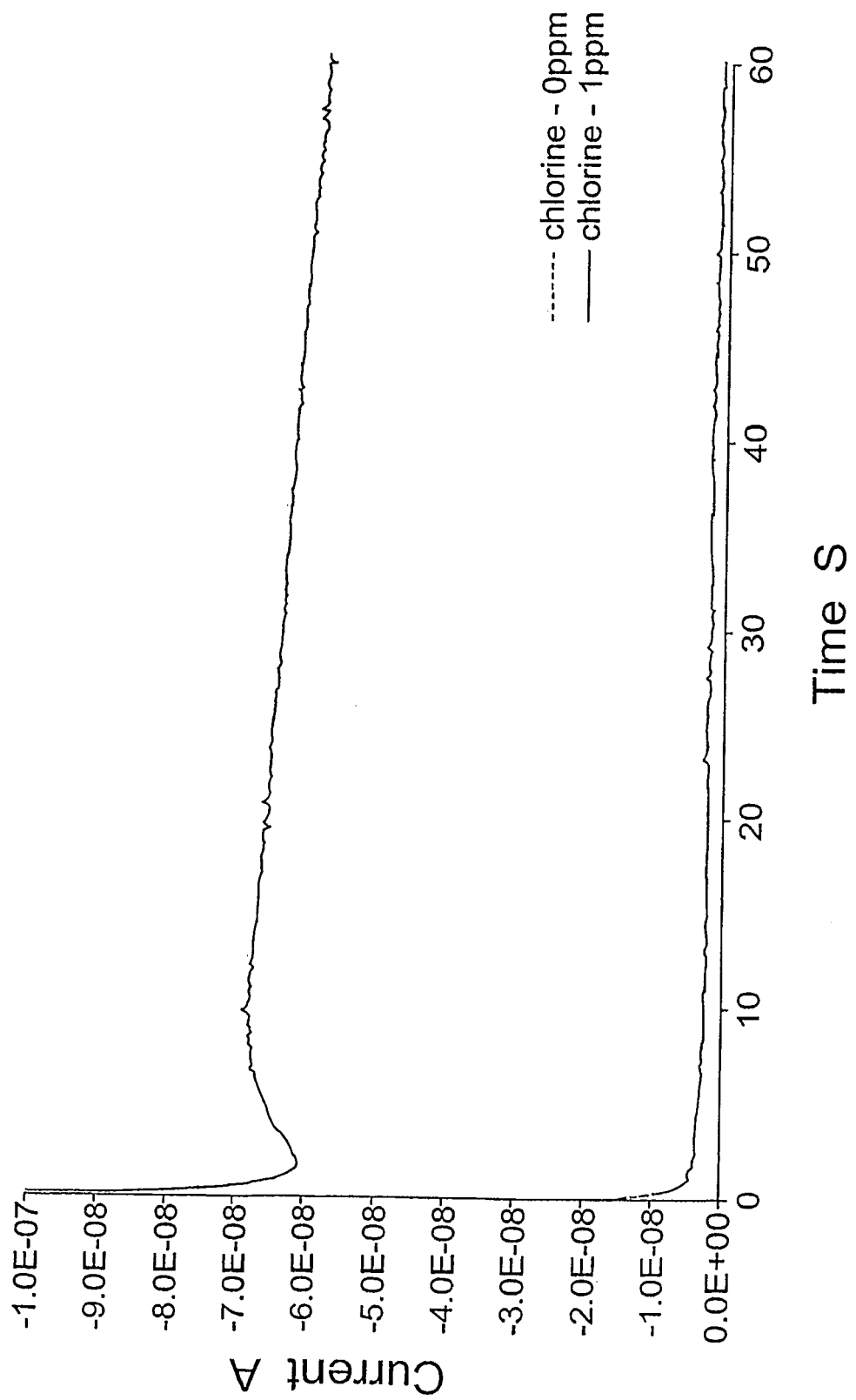
FIG. 2 is a plot of current versus time for 0 ppm and 1 ppm chlorine using a free chlorine electrode.

The electrode shown in FIGS. 1(a) and (b) comprises a support strip composed of insulated polymeric material (1) and a silver or other metallic conductive track (2) deposited on the strip (1). The polymer layer may comprise polyester, polycarbonate or polyvinyl chloride. Each layer is deposited on the plastic substrate by screen printing (also known as silk screen printing or thick film printing). Other suitable processes for deposition of the layers include lithography, vapour deposition, spray coating and vacuum deposition. The first layer consists of four parallel conductive tracks (2) deposited using a highly conductive printable ink formulation. A silver based ink or a silver/silver chloride based ink may be used. One of the four tracks acts as a reference electrode (6). Two working electrodes (7, 8) and a counter electrode (5) are formed by depositing parallel rectangles of another conducting ink (4) over the silver tracks. The conducting ink (4) in this case may be carbon but gold or other metal may be employed. The preferred shape of the electrodes in rectangular but any convenient shape, for example square or circular may be used. The final printing stage involves the deposition of an electrically insulating material over the carbon electrodes. The insulating layer has a number of apertures, (9), for example 95 or more, that exposed the underlying carbon electrode to provide a corresponding array of 95 or more carbon electrodes. The apertures (9) were all of the same size and had a diameter of 200 µM. Electrodes having smaller aperture sizes in the range 50 to 400 µM may be used. The apertures (9) are preferable round but may have any convenient shape.

In a preferred embodiment adapted to simultaneously measure free and total chlorine, liquid reagents are deposited into the reagent layer (10) of each working electrode using a liquid dispensing system. A Biodot AD32000 platform and Biojet Plus 3000 dispensing system may be employed. The total chlorine measuring electrode may have a reagent layer impregnated with potassium iodide (4% w/v) and potassium phthalate (0.1M, pH4) and hydroxyl-ethyl cellulose (0.5% w.v.).

Although free chlorine can be measured directly at a carbon electrode, the kinetics of the reaction are poor and a large over-voltage is required. This leads to a high background signal, poor sensitivity and an increased chance of interference from other reduceable species which may be present in the analyte. To overcome this problem, a redox indicator, for example, DPD or tetramethylbenzidine (TMB), that reacts to the free chlorine may be employed. TMB is preferred because of the stability in solution. A solution used to impregnate a free chlorine electrode contains TMB (1 mg/ml), sodium phosphate buffer (0.2M, pH7) and polyvinylpyrrolidone (1%).

In use of the electrode a voltage of −0.2V versus the printed reference electrode was applied and the current from each working electrode was monitored for 60 seconds by chronoamperometry. The results are shown in FIG. 2. The analytical response was calculated by integrating the current over part or all of the test period. A fuseable link may be incorporated into each sensor so that the sensor can only be used once.

The invention claimed is:

1. An electrochemical sensor comprising a mounting having a screen printed array of electrodes located thereon, the array comprising a reference electrode, a counter electrode, and a plurality of working electrodes,
    wherein the working electrodes include a first working, electrode and a second working electrode that are each overlaid with an insulating layer of insulating material, the insulating layer of each of the first and second electrodes having an array of apertures exposing a respective array of working regions of the working electrodes,
    wherein the first working electrode includes a first reagent layer that overlies the apertures within the insulating layer, the first reagent layer being impregnated with potassium iodide and a phthalate buffer, and
    the second working electrode includes a second reagent layer that overlies the apertures within the insulating layer, the second reagent layer being impregnated with TMB and a buffer.

2. The sensor as claimed in claim 1, the sensor being operable for at least one of detection and assay of an analyte.

3. The sensor as claimed in claim 2, wherein the analyte is at least one form of chlorine.

4. The sensor as claimed in claim 3, wherein the sensor is operable to simultaneously determine the presence of at least one of free and total chlorine and free and combined chlorine.

5. The sensor as claimed in claim 1, wherein a conductive polymer is present on the working electrodes or a conductive polymer layer has been printed onto the sensor containing conductive ink as the working electrodes.

6. The sensor as claimed in claim 1, wherein the working electrodes include carbon.

7. The sensor as claimed in claim 6, wherein the working electrodes are screen printed.

8. The sensor as claimed in claim 1, wherein the reference electrode, two working electrodes and the counter electrode are arranged as four generally parallel tracks.

9. The sensor as claimed in claim 1, wherein the sensor is disposable by the inclusion therein of a fuseable ink.

10. The sensor as claimed in claim 1, further comprising a laminar sheet or strip of insulating polymeric material upon which successive layers have been applied by screen printing.

11. The sensor as claimed in claim 1, wherein the apertures in the array have a dimension of 50 to 400 IJM.

12. The sensor as claimed in claim 11, wherein the dimension is 100 to 200 μM.

13. The sensor as claimed in claim 1, wherein the apertures are circular.

14. The sensor as claimed in claim 1, wherein the array comprises 100 to 500 apertures.

15. The sensor as claimed in claim 14, wherein the array comprises 50 to 200 apertures.

16. The sensor as claimed in claim 9, wherein the array comprises 80 to 120 apertures.

17. The sensor as claimed in claim 16, wherein the array comprises 95 apertures.

18. The sensor as claimed in claim 1, wherein a plurality of tracks of highly conductive printable ink have been screen printed onto the sensor, each in contact with an electrical contact of the sensor.

19. The sensor as claimed in claim 18, wherein the ink includes either silver or silver chloride.

20. The sensor as claimed in claim 18, wherein the working electrodes deposited on the tracks include carbon or gold.

21. The sensor as claimed in claim 1, wherein the reagent layers each comprise a porous layer.

22. The sensor as claimed in claim 1, wherein the sensor is operable as an assay of total chlorine present in a test solution.

23. The sensor as claimed in claim 1, wherein the phthalate buffer is potassium acid phthalate.

24. The sensor as claimed in claim 1, wherein the buffer is a phosphate buffer.

25. The sensor as claimed in claim 24, wherein the reagent layers each further comprises comprise at least one of polyvinylpyrrolidone and hydroxyethylcellulose.

26. The sensor as claimed in claim 1, wherein the reagent layers are deposited by screen printing or microdosing.

* * * * *

UNITED STATES PATENT AND TRADEMARK OFFICE
CERTIFICATE OF CORRECTION

| | | |
|---|---|---|
| PATENT NO. | : 8,142,641 B2 | Page 1 of 1 |
| APPLICATION NO. | : 11/991191 | |
| DATED | : March 27, 2012 | |
| INVENTOR(S) | : Stephen William Birch et al. | |

It is certified that error appears in the above-identified patent and that said Letters Patent is hereby corrected as shown below:

Column 1, line 49, "knows ad" should be --known as--
Column 1, line 56, "knows" should be --known--
Column 2, line 35, the arrow should be inserted into this equation: $I_2 + 2e^- \dashrightarrow 2I^-$
Column 6, line 18, "comprise" should be removed Signed and Sealed this
Fifteenth Day of May, 2012

David J. Kappos
*Director of the United States Patent and Trademark Office*